United States Patent [19]  
Hirai et al.

[11] 4,153,689  
[45] May 8, 1979

[54] STABLE INSULIN PREPARATION FOR NASAL ADMINISTRATION

[75] Inventors: Shin-Ichiro Hirai, Kawanishi; Toshiaki Ikenaga, Takatsuki; Tai Matsuzawa, Suita, all of Japan

[73] Assignee: Takeda Chemical Industries, Ltd., Osaka, Japan

[21] Appl. No.: 824,955

[22] Filed: Aug. 15, 1977

Related U.S. Application Data

[63] Continuation of Ser. No. 686,220, May 12, 1976, abandoned.

[30] Foreign Application Priority Data

Jun. 13, 1975 [GB] United Kingdom ............... 25351/75

[51] Int. Cl.² ............................................. A61K 37/26

[52] U.S. Cl. .................................... 424/178; 424/359
[58] Field of Search ................................ 424/178, 359

[56] References Cited

U.S. PATENT DOCUMENTS 2,055,083  9/1936  Klein et al. .......................... 424/178

OTHER PUBLICATIONS

Jensen–*Insulin* (1938), New York–The Commonwealth Fund, Oxford Univ. Press, pp. 92–98.

Primary Examiner—V. D. Turner  
Attorney, Agent, or Firm—Wenderoth, Lind & Ponack

[57] ABSTRACT

Nasal administration of insulin is achieved by the use of an aqueous solution whose pH value is not higher than 4.7.

45 Claims, No Drawings

STABLE INSULIN PREPARATION FOR NASAL ADMINISTRATION

This application is a continuation of application Ser. No. 686,220, filed May 12, 1976 (now abandoned).

The present invention relates to a novel insulin preparation. More particularly, the present invention relates to an insulin preparation which is clinically suitable to nasal administration. The present invention also relates to a novel method for administration of insulin.

It has hitherto been known that insulin is useful as a medicine for diabetes mellitus, shock therapy in psychiatric disorders, and the treatment of malnutrition.

Insulin has hitherto been administered solely by injection. Other kinds of administration of insulin, e.g. sublingual administration, oral administration, intratracheal administration and rectal administration have been studied since the discovery of insulin. However, as insulin is a polypeptide comprising about 50 amino acids and having a molecular weight of about 6000, it has hitherto been acknowledged that little or no pharmacological effect of insulin is achieved by any of those administration methods other than injection (see "Insulin Monogatari", page 86, published by Iwanami-shoten in Japan in 1965).

There have also been reported long-acting insulin preparations containing zinc or protamine. However, in the case of these preparations, a considerable amount of insulin enters into the patient's blood stream all the time, and therefore a dangerous hypoglycemic shock may occur when a patient suffering from diabetes mellitus is hungry or asleep. Thus, it is believed that insulin should be administered to a patient three times a day right after food intake to escape the hypoglycemic shock (The Journal of Practical Pharmacy, 25, 505 (1974)). However, it is difficult to administer insulin by means of an injection according to the above dosage schedule on account of the physical pain and the mental suffering involved.

We have sought to find out a novel administration method for insulin as well as an insulin preparation which is free from such disadvantages, and we have unexpectedly found that, when an aqueous insulin solution of which the pH is not more than 4.7 is contacted with the nasal mucous membrane, insulin is rapidly absorbed through the membrane into the blood stream. This phenomenon was confirmed by the fact that the concentration of plasma glucose is remarkably decreased soon after the nasal administration of insulin.

We have also found that a preferred absorption of insulin is attained when the aqueous insulin solution is contacted with the nasal membrane in the form of a spray.

We have further found that the dose of insulin by nasal administration required for producing a decrease in plasma glucose which is the same as that obtained by the intramuscular administration is from 5 to 10 times greater than the dose of insulin by intramuscular administration.

Thus we have found that nasal administration established a new self-medication of insulin, and such a medication overcomes the disadvantages of the hitherto known insulin therapy.

However, insulin in an aqueous solution is very unstable and tends to degrade in an acid medium to deaminated products [Journal of Biological Chemistry 237, 3406]. Furthermore, during storage of the aqueous insulin solution, gelatinization and precipitation are observed. In order to improve the stability of insulin preparations in these respects, we have made further studies.

As a result, we have now found that an aqueous insulin solution having a pH value within the range of from 2.5 to 4.7, which comprises 0.1 to 10 weight % of insulin and 0.1 to 20 weight % of (1) one or more non-ionic surface-active agents whose hydrophile-lipophile balance value is in the range of from 9 to 22 (i.e. from 9:1 to 22:1) and/or (2) polyethylene glycol whose molecular weight is in the range of from 200 to 7500 as a stabilizing agent is a preparation which overcomes the above disadvantages of the hitherto known aqueous insulin preparations, and the resulting new insulin preparation is highly suitable to the nasal administration of insulin.

Insulin to be employed in the present invention may be obtained from natural sources such as mammals (e.g. pigs or cattle), birds or fish, or by chemical reactions according to the known processes chosen. Furthermore, the insulin which may be used in this invention may include a small amount of harmless impurities. A highly purified insulin which is called a "monocomponent" is of course also useful in this invention.

The non-ionic surface-active agents are exemplified by a polyoxyethylene fatty acid ester, a polyoxyethylene higher alcohol ether, a polyoxyethylene polyoxypropylene higher alcohol ether, a polyoxyethylene sorbitan fatty acid ester, a polyoxyethylene alkylphenyl ether, or a polyoxyethylene hydrogenated castor oil. These non-ionic surface active agents may be used alone or in combination. The non-ionic surface-active agents may be conveniently chosen from those known per se.

In particular, a polyoxyethylene fatty acid ester represented by the formula: $RCOO-(CH_2CH_2O)_nH$ [wherein R is a saturated or unsaturated alkyl group of from 7 to 17 carbon atoms, and n is an integer of from 10 to 60]; a polyoxyethylene higher alcohol ether represented by the formula: $R-O-(CH_2CH_2O)_nH$ [wherein R is a saturated or unsaturated alkyl group of from 4 to 18 carbon atoms, and n is an integer of from 3 to 60]; a polyoxyethylene polyoxypropylene higher alcohol ether represented by the formula: $R-O-(CH_2CH_2O)_m(CH_2CH_2O)_nH$ [wherein R is a saturated or unsaturated alkyl of from 12 to 18 carbon atoms, m is an integer of from 1 to 10, and n is an integer of from 10 to 40]; a polyoxyethylene sorbitan fatty acid ester represented by the formula: $RCOO-C_6H_8O_4-(CH_2CH_2O)_nH$ [wherein R is a saturated or unsaturated alkyl of from 7 to 17 carbon atoms, and n is an integer of from 10 to 20]; polyoxyethylene alkylphenyl ether represented by the formula:

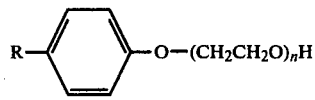

[wherein R is a saturated or unsaturated alkyl of from 8 to 12 carbon atoms, and n is an integer of from 8 to 70]; and a polyoxyethylene hydrogenated castor oil represented by the formula: $C_3H_5(COOC_{17}H_{34}O)_3-(CH_2CH_2O)_nH$ [wherein n is an integer of from 20 to 120] are preferred on account of their low cost.

When one non-ionic surface-active agent is used, a non-ionic surface active agent whose hydrophile-lipophile balance value is in the range of from 9 to 22 is chosen, preferably among the above non-ionic surface active agent. When two or more non-ionic surface active agents are used, the non-ionic surface-active agents are chosen and combined so that the hydrophile-lipophile balance value of the mixture falls within the range of from 9 to 22.

Polyethylene glycol may be used instead of, or in combination with, one or more non-ionic surface-active agents. The molecular weight of polyethylene glycol is usually in the range of from 200 to 7500, and more preferably in the range of from 600 to 7500.

The insulin content in the aqueous preparation of this invention is usually in the range of from 0.1 to 10 weight %, and preferably in the range of from 0.2 to 5 weight %. When the insulin content is less than 0.1 weight %, the absorption of insulin through the nasal mucous membrane is insufficient. When the insulin content is more than 10 weight %, precipitation occurs.

The pH value of the insulin preparation of this invention is usually in the range of from 2.5 to 4.7, preferably in the range of from 2.8 to 4.0. When the pH value of the preparation is less than 2.5, the decomposition of insulin in the preparation is accelerated in the course of storage.

The content of one or more non-ionic surface-active agents and/or polyethylene glycol is usually in the range of from 0.1 to 20 weight %, and preferably in the range of from 0.5 to 10 weight %. The content of less than 0.1 weight % is not enough to overcome the problem of the gelatinisation, precipitation and decomposition of insulin. Although the content of more than 20 weight % also give a satisfactory effect, it is not practical from an economical point of view.

The aqueous insulin preparation of this invention may be produced by mixing the ingredients in optional order according to conventional means. Usually, the preparation is produced by dissolving insulin and one or more non-ionic surface-active agents and/or polyethylene glycol in water (more preferably water containing an acid, e.g. hydrochloric acid), in the above-mentioned ratios of the ingredients, and adjusting the pH value of the aqueous solution to the above-mentioned range with a base (e.g. an aqueous sodium hydroxide solution) or an acid (e.g. hydrochloric acid).

Furthermore, if desired, the insulin preparation of this invention may contain other conventional ingredients for aqueous medicaments, e.g. an isotonic agent, an antiseptic agent, a preservative, or a buffer.

As regards the manner of the insulin administration of this invention, the aqueous insulin solution of this invention may be applied to nasal cavities in the form of a spray by using an atomiser, a nebuliser or a sprayer, and the spray of the insulin solution is contacted with the nasal mucous membrane.

The most prominent merit of such nasal administration of this invention is that it enables all kinds of patients (e.g. human) requiring the insulin treatment to take insulin by self-medication easily at the desired time without any troubles, e.g. pain etc.

According to the present invention, the dose of insulin for the nasal use in terms of the weight of insulin is about 5 to 10 times as compared with that of the intramuscular injection.

The invention is illustrated by the following examples.

EXAMPLE 1

In 5 ml of 0.1 N hydrochloric acid are dissolved 200 mg of pork insulin (about 25 units per mg), then 100 mg of polysorbate 80 and 160 mg of glycerin are added. The solution is adjusted to pH 3.1 with 0.1 N aqueous sodium hydroxide solution and 0.1 N hydrochloric acid and diluted with distilled water to 10 ml.

The resulting solution has an insulin potency of 500 units per ml.

EXAMPLE 2

In 5 ml of pH 3.5 sodium citrate buffer are dissolved 500 mg of beef insulin (about 25 units per mg), and 300 mg of polyoxyethylene 9 lauryl ether and 500 mg of glucose are then added. The solution is adjusted to pH 3.5 with 0.1 N aqueous sodium hydroxide solution and 0.1 N hydrochloric acid, and is diluted with distilled water to 10 ml.

The resulting solution has an insulin potency of 1250 units per ml.

EXAMPLE 3

In 8 ml of 0.01 N hydrochloric acid are dissolved 40 mg of beef insulin (about 25 units per mg), and 500 mg of polyoxyethylene 50 hydrogenated castor oil (NIK-KOL HCO-50 ®) are then added. The solution is adjusted to pH 3.0 with 0.1 N aqueous sodium hydroxide solution and 0.1 N hydrochloric acid, and is diluted with distilled water to 10 ml.

The resulting solution has an insulin potency of 100 units per ml.

EXAMPLE 4

In 5 ml of 0.1 N hydrochloric acid are dissolved 100 mg of pork insulin (about 25 units per mg), and 500 mg of polyethylene glycol 4000 (Carbowax 4000 ®) are added. The solution is adjusted to pH 3.5 with 0.1 N aqueous sodium hydroxide solution and 0.1 N hydrochloric acid, and is diluted with distilled water to 10 ml.

The resulting solution has an insulin potency of 250 units per ml.

TEST 1

Relationship between dose and pharmacological effect

Stable insulin preparations for nasal use prepared by the same procedure as in Example 1, in which only insulin contents were varied, were used for this examination. Adult beagle dogs weighing approximately 9 kg. were used to examine the nasal and intramuscular absorption of insulin. The former examination was made by applying 0.1 ml of the insulin preparation to the nasal cavity with a nebuliser under anaesthesis with pentobarbital. The latter examination was made by injecting the insulin solution intramuscularly at the thigh.

To determine the plasma glucose, blood samples were drawn at timed intervals after the drug administration and the plasma samples were assayed by a method using otoluidine. (Clin. Chem. 8, 215(1962)).

The results obtained are shown in Table 1 below, representing the change in plasma glucose following insulin administration. Each value represents the average of the four animals.

Table 1

| Method of Administration | Dose amount (unit/dog) | Change in Plasma Glucose, % | | | | | | |
|---|---|---|---|---|---|---|---|---|
| | | 0 | 0.5 | 1 | 2 | 3 | 4 | 6(hr.) |
| | 50 | 100 | 48.4 | 28.0 | 24.7 | 33.8 | 47.8 | 69.7 |

Table 1-continued

| Method of Administration | Dose amount (unit/dog) | Change in Plasma Glucose, % | | | | | | |
|---|---|---|---|---|---|---|---|---|
| | | 0 | 0.5 | 1 | 2 | 3 | 4 | 6(hr.) |
| Nasal Administration | 25 | 100 | 62.9 | 29.0 | 27.8 | 54.5 | 70.5 | 99.2 |
| | 12.5 | 100 | 64.0 | 28.1 | 37.3 | 89.0 | 86.1 | 86.4 |
| | 8 | 100 | 67.2 | 39.2 | 56.0 | 72.1 | 84.3 | 81.1 |
| | 5 | 100 | 74.2 | 55.8 | 65.8 | 86.0 | 86.1 | 91.7 |
| | 2 | 100 | 80.9 | 79.9 | 99.3 | 90.6 | 92.3 | 85.0 |
| Intramuscular Administration | 1 | 100 | 76.1 | 57.1 | 44.0 | 51.5 | 64.5 | 77.3 |
| | 0.5 | 100 | 89.1 | 74.6 | 69.2 | 80.0 | 81.7 | 73.3 |

TEST 2

Effect of the pH of the insulin preparation of the pharmacological effect

The stable insulin preparations for this examination were obtained by the same procedure as in Example 1, in which however polysorbate 80 was not added and the pH of the insulin preparation was varied with 0.1 N aqueous sodium hydroxide solution and 0.1 N hydrochloric acid. The dose of the insulin was fixed at 50 units per dog. The methods of nasal administration and the determination of the plasma glucose were carried out according to the procedure described in Test 1. The results obtained are shown in Table 2 below:

Table 2

| pH | Change in Plasma Glucose, % | | | | | | |
|---|---|---|---|---|---|---|---|
| | 0 | 0.5 | 1 | 2 | 3 | 4 | 6(hr.) |
| 3.1 | 100 | 48.4 | 28.0 | 24.7 | 33.8 | 47.8 | 69.7 |
| 3.7 | 100 | 64.6 | 28.7 | 25.7 | 41.4 | 64.7 | 87.9 |
| 4.7 | 100 | 85.2 | 66.0 | 64.5 | 71.9 | 76.1 | 70.6 |
| 5.2 | 100 | 75.3 | 79.3 | 89.4 | 91.8 | 94.1 | 90.3 |
| 6.1 | 100 | 95.9 | 96.9 | 98.0 | 90.4 | 94.9 | 91.7 |

TEST 3

Stability of the insulin preparation

The insulin preparations for this examination were obtained by the same procedure as in Example 3, in which the non-ionic surface-active agent was replaced by other agents and the pH of the insulin preparation was varied. The solution was transferred to a 2 ml white ampoule and the ampoule was fused and placed in a thermostatically controlled bath at 80° C. The occurrence of precipitation or gelatinization in the insulin preparation was examined as a function of time. The result obtained was shown in Table 3.

Table 3

| pH | Stabilizing agent | Duration of Heating at 80° C. | | | | | |
|---|---|---|---|---|---|---|---|
| | | 3 | 5 | 10 | 15 | 20 | 30(hr.) |
| 2.8 | Polyoxyethylene 50 hydrogenated castor oil | — | — | — | + | +G | |
| | Polyoxyethylene 9 lauryl alcohol ether | — | — | — | + | +G | |
| | Control* | — | ++G | ++G | ++G | ++G | |
| 3.0 | Polyoxyethylene 50 hydrogenated castor oil | — | — | — | — | — | |
| | Polysorbate 80 | — | — | — | — | — | |
| | Polyoxyethylene 9 lauryl alcohol ether | — | — | — | — | — | — |
| | Polyoxyethylene 40 stearic acid ester | — | — | — | — | — | — |
| | Polyethylene glycol 400 | — | — | — | — | — | — |
| | Control* | — | — | — | +G | ++G | ++G |

Remarks:
*No stabilizing agent
— no precipitate
+ slight precipitate
++ precipitate
G gelatinizing

We claim:

1. A stable aqueous insulin solution having a pH value in the range of from 2.5 to 4.7, which comprises 0.1 to 10 weight percent of insulin and as a stabilizing agent 0.1 to 20 weight percent of a member selected from the group consisting of (a) at least one non-ionic surface-active agent whose hydrophile/lipophile balance value is in the range of from 9 to 22, (b) polyethylene glycol having a molecular weight in the range of from 200 to 7500 and (c) mixtures of (a) and (b).

2. A stable aqueous insulin solution having a pH value in the range of from 2.5 to 4.7, which comprises 0.2 to 5 weight percent of insulin and as a stabilizing agent 0.1 to 20 weight percent of a member selected from the group consisting of (a) at least one non-ionic surface-active agent whose hydrophile/lipophile balance value is in the range of from 9 to 22, (b) polyethylene glycol having a molecular weight in the range of from 200 to 7500 and (c) mixtures of (a) and (b).

3. A stable aqueous insulin solution having a pH value in the range of from 2.8 to 4.0, which comprises 0.1 to 10 weight percent of insulin and as a stabilizing agent 0.1 to 20 weight percent of a member selected from the group consisting of (a) at least one non-ionic surface-active agent whose hydrophile/lipophile balance value is in the range of from 9 to 22, (b) polyethylene glycol having a molecular weight in the range of from 200 to 7500 and (c) mixtures of (a) and (b).

4. A stable aqueous insulin solution having a pH value in the range of from 2.8 to 4.0, which comprises 0.2 to 5 weight percent of insulin and as a stabilizing agent 0.1 to 20 weight percent of a member selected from the group consisting of (a) at least one non-ionic surface-active agent whose hydrophile/lipophile balance value is in the range of from 9 to 22, (b) polyethylene glycol having a molecular weight in the range of from 200 to 7500 and (c) mixtures of (a) and (b).

5. A stable aqueous insulin solution as in claim 4, wherein the stabilizing agent is polyoxyethylene 50 hydrogenated castor oil.

6. A stable aqueous insulin solution as in claim 4, wherein the stabilizing agent is polyoxyethylene 40 stearic acid ester.

7. A stable aqueous insulin solution as in claim 4, wherein the stabilizing agent is polyethylene glycol 4000.

8. A stable aqueous insulin solution as in claim 4, wehrein the stabilizing agent is polyoxyethylene 9 lauryl ether.

9. A stable aqueous insulin solution according to claim 4 wherein the insulin is that obtained from natural sources.

10. A stable aqueous insulin solution according to claim 4 wherein the insulin is that produced synthetically.

11. A stable aqueous insulin solution according to claim 4 wherein the insulin is a monocomponent.

12. A stable aqueous insulin solution according to claim 4 wherein the non-ionic surface-active agents are selected from the group consisting of a polyoxyethylene fatty acid ester, a polyoxyethylene higher alcohol ether, a polyoxyethylene polyoxypropylene higher alcohol ether, a polyoxyethylene sorbitan fatty acid ester, a polyoxyethylene alkylphenyl ether, and a polyoxyethylene hydrogenated castor oil.

13. A stable aqueous insulin solution according to claim 4 wherein a mixture of non-ionic surface active agents is employed, said agents being chosen so that the combined hydrophile/lipophile balance value of the mixture falls within the range of from 9 to 22.

14. A stable, aqueous insulin solution according to claim 4, wherein the stabilizing agent is polysorbate 80.

15. A stable aqueous insulin solution as in claim 1 wherein the stabilizing agent is a polyoxyethylene fatty acid ester of the formula

RCOO—(CH$_2$CH$_2$O)$_n$H wherein R is a saturated or unsaturated alkyl group of from 7 to 17 carbon atoms, and n is an integer of from 10 to 60.

16. A stable aqueous insulin solution as in claim 1 wherein the stabilizing agent is polyoxyethylene higher alcohol ether of the formula

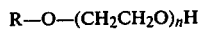
R—O—(CH$_2$CH$_2$O)$_n$H wherein R is a saturated or unsaturated alkyl group of from 4 to 18 carbon atoms, and n is an integer of from 3 to 60.

17. A stable aqueous insulin solution as in claim 1 wherein the stabilizing agent is a polyoxyethylene polyoxypropylene higher alcohol ether of the formula

R—O—(CH$_2$CH$_2$CH$_2$O)$_m$(CH$_2$CH$_2$O)$_n$H wherein R is a saturated or unsaturated alkyl of from 12 to 18 carbon atoms, m is an integer of from 1 to 10 and n is an integer of from 10 to 40.

18. A stable aqueous insulin solution as in claim 1 wherein the stabilizing agent is a polyoxyethylene sorbitan fatty acid ester of the formula

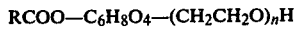
RCOO—C$_6$H$_8$O$_4$—(CH$_2$CH$_2$O)$_n$H wherein R is a saturated or unsaturated alkyl of from 7 to 17 carbon atoms, and n is an integer of from 10 to 20.

19. A stable aqueous insulin solution as in claim 1 wherein the stabilizing agent is a polyoxyethylene alkylphenyl ether of the formula

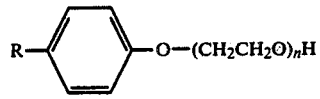

wherein R is a saturated or unsaturated alkyl of from 8 to 12 carbon atoms, and n is an integer of from 8 to 70.

20. A stable aqueous insulin solution as in claim 1 wherein the stabilizing agent is a polyoxyethylene hydrogenated castor oil of the formula

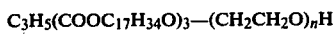
C$_3$H$_5$(COOC$_{17}$H$_{34}$O)$_3$—(CH$_2$CH$_2$O)$_n$H wherein n is an integer of from 20 to 120.

21. A stable aqueous insulin solution as in claim 1 wherein the stabilizing agent is polyethylene glycol having a molecular weight in the range of from 200 to 7500.

22. A stable aqueous insulin solution as in claim 21 wherein the molecular weight of the polyethylene glycol is in the range of from 600 to 7500.

23. A method for the treatment of diabetes mellitus which comprises administering in the form of a spray through the nasal mucous membrane of a patient suffering from diabetes mellitus a pharmaceutically effective amount of an aqueous, insulin solution whose pH value is not higher than 4.7.

24. A method according to claim 23 wherein the pH range of the solution is from 2.5 to 4.0.

25. A method according to claim 23 wherein the pH range of the solution is from 2.8 to 4.0.

26. A method for the treatment of diabetes mellitus which comprises administering through the nasal mucous membrane of a patient suffering from diabetes mellitus a pharmaceutically effective amount of a stable, aqueous insulin solution having a pH value in the range of from 2.5 to 4.7 which comprises 0.1 to 10 weight percent of insulin and as a stabilizing agent 0.1 to 20 weight percent of a member selected from the group consisting of (a) at least one nonionic surface-active agent whose hydrophile/lipophile balance is in the range of from 9 to 22, (b) polyethylene glycol having a molecular weight in the range of from 200 to 7500 and (c) mixtures of (a) and (b).

27. A method according to claim 26 wherein the aqueous insulin solution is administered in the form of a spray.

28. A method for the treatment of diabetes mellitus which comprises administering in the form of a spray through the nasal mucous membrane of the patient suffering from diabetes mellitus a pharmaceutically acceptable amount of a stable aqueous insulin solution having a pH value in the range of from 2.8 to 4.0 which comprises 0.2 to 5 weight percent of insulin and as a stabilizing agent 0.1 to 20 weight percent of a member selected from the group consisting of (a) at least one nonionic surface-active agent whose hydrophile/lipophile balance value is in the range of from 9 to 22, (b) polyethylene glycol having a molecular weight in the range of from 200 to 7500 and (c) mixtures of (a) and (b).

29. A method according to claim 26 wherein the stabilizing agent is a polyoxyethylene fatty acid ester of the formula

RCOO—(CH$_2$CH$_2$O)$_n$H wherein R is a saturated or unsaturated alkyl group of from 7 to 17 carbon atoms, and n is an integer of from 10 to 60.

30. A method according to claim 26 wherein the stabilizing agent is polyoxyethylene higher alcohol ether of the formula

R—O—(CH$_2$CH$_2$O)$_n$H wherein R is a saturated or unsaturated alkyl group of from 4 to 18 carbon atoms, and n is an integer of from 3 to 60.

31. A method according to claim 26 wherein the stabilizing agent is a polyoxyethylene polyoxypropylene higher alcohol ether of the formula

R—O—(CH$_2$CH$_2$CH$_2$O)$_m$(CH$_2$CH$_2$O)$_n$H wherein R is a saturated or unsaturated alkyl of from 12 to 18 carbon atoms, m is an integer of from 1 to 10 and n is an integer of from 10 to 40.

32. A method according to claim 26 wherein the stabilizing agent is a polyoxyethylene sorbitan fatty acid ester of the formula

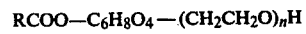

RCOO—C$_6$H$_8$O$_4$—(CH$_2$CH$_2$O)$_n$H wherein R is a saturated or unsaturated alkyl of from 7 to 17 carbon atoms, and n is an integer of from 10 to 20.

33. A method according to claim 26 wherein the stabilizing agent is a polyoxyethylene alkylphenyl ether of the formula

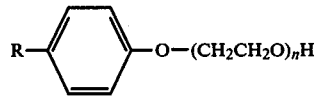

wherein R is a saturated or unsaturated alkyl of from 8 to 12 carbon atoms, and n is an integer of from 8 to 70.

34. A method according to claim 26 wherein the stabilizing agent is a polyoxyethylene hydrogenated castor oil of the formula

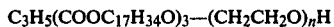

C$_3$H$_5$(COOC$_{17}$H$_{34}$O)$_3$—(CH$_2$CH$_2$O)$_n$H wherein n is an integer of from 20 to 120.

35. A method according to claim 26 wherein the stabilizing agent is polyethylene glycol having a molecular weight in the range of from 200 to 7500.

36. A method according to claim 35 wherein the molecular weight of the polyethylene glycol is in the range of from 600 to 7500.

37. A method according to claim 28 wherein the stabilizing agent is polyoxyethylene 50 hydrogenated castor oil.

38. A method according to claim 28 wherein the stabilizing agent is polyoxyethylene 40 stearic acid ester.

39. A method according to claim 28 wherein the stabilizing agent is polyethylene glycol 4000.

40. A method according to claim 28 wherein the stabilizing agent is polyoxyethylene 9 lauryl ether.

41. A method according to claim 28 wherein the insulin is that obtained from natural sources.

42. A method according to claim 28 wherein the insulin is that produced synthetically.

43. A method according to claim 28 wherein the insulin is a mono-component.

44. A method according to claim 28 wherein the nonionic surface-active agents are selected from the group consisting of a polyoxyethylene fatty acid ester, a polyoxyethylene higher alcohol ether, a polyoxyethylene polyoxypropylene higher alcohol ether, a polyoxyethylene sorbitan fatty acid ester, a polyoxyethylene alkylphenyl ether, and a polyoxyethylene hydrogenated castor oil.

45. A method according to claim 28 wherein a mixture of nonionic surface-active agents is employed, said agents being chosen so that the combined hydrophile/lipophile balance value of the mixture falls within the range of 9 to 22.

* * * * *